United States Patent
Flashinski

(10) Patent No.: US 7,341,736 B2
(45) Date of Patent: Mar. 11, 2008

(54) AEROSOL SPRAY RESISTANT TO DISCOLORATION

(75) Inventor: Stanley J. Flashinski, Racine, WI (US)

(73) Assignee: S.C. Johnson & Son, Inc., Racine, WI (US)

(*) Notice: Subject to any disclaimer, the term of this patent is extended or adjusted under 35 U.S.C. 154(b) by 827 days.

(21) Appl. No.: 10/768,346

(22) Filed: Jan. 30, 2004

(65) Prior Publication Data

US 2005/0169953 A1    Aug. 4, 2005

(51) Int. Cl.
*A01N 25/32* (2006.01)
*A01N 53/00* (2006.01)

(52) U.S. Cl. .......................... 424/406; 43/45; 43/405; 43/DIG. 11; 514/65; 514/74; 514/531; 514/763; 514/919

(58) Field of Classification Search ............... None
See application file for complete search history.

(56) References Cited

U.S. PATENT DOCUMENTS

| | | | |
|---|---|---|---|
| 5,411,992 A | 5/1995 | Eini et al. | |
| 5,466,674 A | 11/1995 | Preiser et al. | |
| 5,549,902 A | 8/1996 | Preiser et al. | |
| 5,773,016 A | 6/1998 | Nelson | |
| 5,792,465 A | 8/1998 | Hagarty | |
| 5,871,765 A | 2/1999 | Johnson et al. | |
| 5,965,674 A | 10/1999 | Moen et al. | |
| 6,067,634 A | 5/2000 | Nelson | |
| 6,111,055 A | 8/2000 | Berger et al. | |
| 6,171,608 B1 | 1/2001 | Schmitt et al. | |
| 6,183,765 B1 | 2/2001 | Kalder et al. | |
| 6,242,509 B1 | 6/2001 | Berger et al. | |
| 6,264,939 B1 | 7/2001 | Light et al. | |
| 6,296,865 B1 | 10/2001 | Dujardin et al. | |
| 6,440,406 B1 | 8/2002 | Lopez, Jr. et al. | |
| 6,488,916 B1 | 12/2002 | Fowler | |
| 2002/0173436 A1 | 11/2002 | Sonnenberg et al. | |
| 2003/0005484 A1 | 1/2003 | Crandall, Jr. et al. | |
| 2003/0096878 A1 | 5/2003 | Harper et al. | |
| 2003/0136748 A1 | 7/2003 | Braithwaite | |
| 2005/0069568 A1* | 3/2005 | Hallahan | 424/405 |

FOREIGN PATENT DOCUMENTS

| | | |
|---|---|---|
| GB | 1445813 | 8/1976 |
| WO | WO98/18625 | 11/1998 |
| WO | WO01/18145 A2 | 3/2001 |

OTHER PUBLICATIONS

Page 19 from The Whole Dog Journal, relating to "Spot-On Pesticides And Their Ingredients" (2002).
Database WPI, Section Ch. Week 19914, Derwent Publications, Ltd., London, GB; AN 1991-099128 XP002330264 & JP 03 044305A (Earth Seiyaku KK) Feb. 26, 1991 abstract.

* cited by examiner

*Primary Examiner*—Neil S. Levy

(57) ABSTRACT

Aerosol insecticidal sprays are disclosed that contain butyl-hydroxytoluene, limonene, and sodium benzoate, in addition to water, hydrocarbon solvent, propellant, surfactant, and insecticidal active. The sprays are resistant to discoloration even during long term storage.

9 Claims, No Drawings

AEROSOL SPRAY RESISTANT TO DISCOLORATION

CROSS-REFERENCE TO RELATED APPLICATIONS

Not applicable

STATEMENT REGARDING FEDERALLY SPONSORED RESEARCH/DEVELOPMENT

Not applicable

BACKGROUND OF THE INVENTION

The present invention relates to sprays designed to deliver active ingredients, such as insecticides, fragrancers and cleaners. More particularly it relates to aerosol sprays that contain limonene (for orange fragrance and solvent purposes) as well as additional chemicals to minimize can corrosion and discoloration during storage.

A variety of sprays are known. For example, U.S. Pat. No. 5,773,016 describes aerosol emulsion sprays formed from water, hydrocarbon solvent, surfactant, insecticide(s), and hydrocarbon gas propellant(s). This patent also describes the desirability of adding sodium nitrite, sodium benzoate, or mixtures thereof to reduce can corrosion during storage.

U.S. Pat. No. 5,792,465 described relatively stable microemulsions used to deliver insect control agents, as well as the possibility of adding propane/isobutane mixtures as a preferred propellant. This patent also noted that d-limonene (an element of orange oil) could be added as well, as a solvent.

In separate work it has been suggested to add butylhydroxytoluene ("BHT") to some insecticidal mixtures, primarily for its antioxidant properties (to protect actives).

While the art has therefore suggested the use of limonene in certain sprays, such formulations tend to quickly discolor, particularly in the presence of the anti-corrosive agent sodium nitrite. This can make a consumer less willing to use such a spray in the home, even though orange fragrance is highly desirable.

Hence, a need exists for improved spray formulations containing limonene.

BRIEF SUMMARY OF THE INVENTION

In one aspect the invention provides an aerosol spray that contains at least 20% (preferably about 50%) water, at least 1% (preferably about 10%) hydrocarbon solvent, at least 0.1% (preferably about 1%) surfactant, at least 0.1% (preferably about 2%) limonene, at least 0.01% (preferably about 0.5%) butylhydroxytoluene, at least 0.01% (preferably about 0.2%) alkali metal benzoate (preferably sodium benzoate), and at least 0.01% (preferably about 0.4%) of an active selected from the group consisting of pest control materials (e.g. insecticides, insect repellants or insect control growth regulators), fragrancers, odor masks, and disinfectants. Unless stated to the contrary, all percentages set forth herein are weight percentages. The spray is preferably in the form of an aerosol spray containing a gas propellant.

Preferred hydrocarbon solvents (apart from the gas propellant) have between 6 and 20 carbons. Examples include hexane, benzene, toluene, xylene, mineral spirits, mineral oil, heavy aromatic naptha, kerosene, paraffins, isoparaffins, and other alkanes and alkenes. A particularly preferred hydrocarbons is the Norpar 13 solvent from Exxon.

The surfactants can be chosen from a variety of cationic, anionic, amphoteric and nonionic surfactants known to be useful in connection with aerosol emulsion sprays for delivering actives, with nonionics and anionics being particularly preferred. In this regard it is preferred to use a mixture of sorbitan monooleate and polyethoxylated stearic acid as the surfactants when formulating an insecticidal spray.

Other suitable nonionic surfactants, depending on the active and application, include polyethoxylates derived from primary and secondary aliphatic alcohols having from 8 to 24 carbons atoms in the alcohol alkyl chain. Part or all of the ethylene oxide may be replaced by propylene oxide. Still other suitable nonionic surfactants may include polyoxyalkylene alkyl phenols; polyalkylene esters of the higher organic acids having 8 or more carbon atoms in the acid hydrophobe and 10 or more moles of ethylene oxide as a hydrophilic group; polyalkylene alkyl amines whose hydrophobic group is from a primary, secondary or tertiary amine and whose ethylene oxide content is sufficiently high to impart both water solubility and nonionic characteristics, usually derived from fatty acids with 8 or more carbons; polyalkylene alkyl amides having a hydrophobic group derived from an amide of a fatty acid or ester; fatty acid esters of glycols, polyalkylene oxide block copolymer and the like.

Representative of possible suitable anionic surfactants (depending on active and application) include alkyl aryl sulfonates of 6 to 20 carbons atoms in the alkyl group; $C_{10}$-$C_{22}$ fatty acid soaps; $C_{10}$-$C_{22}$ fatty sulfates; $C_{10}$-$C_{22}$ alkyl sulfonates, including the alkali metal salts of the higher alkyl and linear paraffin sulfonic acids and salts thereof, alkali metal dialkyl sulfosuccinates, ethoxylated alcohol sulfates, phosphate esters, taurates, and the like.

A wide variety of cationic and amphoteric surfactants, of the types conventionally used in aerosol emulsion sprays, can also be used. However, they are not preferred because they tend to be somewhat more corrosive.

A variety of gaseous hydrocarbons can be used as the propellants. For purposes of this application, a "hydrocarbon" only has carbon and hydrogen. They typically liquefy under the pressure conditions of an aerosol can and become part of the hydrocarbon solvent. For example, the propellant can be dimethylether, difluoroethane, propane, butane, isobutane and mixtures thereof (preferably an isobutane/propane mix). A particularly preferred propellant is A-46 from Phillips Petroleum, a 80/20 mol % propane/isobutane mixture. Alternatively, the propellant could be another type of gas such as $CO_2$.

Where the active is a pest control ingredient, such as an ingredient effective against crawling or flying insects, the active may be a mixture of synthetic pyrethroids such as two or more of tetramethrin, permethrin, cypermethrin, cyfluthrin, allethrin forte, phenothrin, d-phenothrin, resmethrin, esbiothrin, allethrin, d-trans allethrin and kadethrin, and lambda-cyhalothrin, natural pyrethrum (e.g. pyrethrins), and organo phosphates such as chlorpyrifos See also other insecticides listed in U.S. Pat. No. 5,037,653. Various synergists, such as piperonyl butoxide, may also be used.

The insect control agent can instead be a repellent such as citronella, lemon grass oil, lavender oil, cinnamon oil, neem oil, clove oil, sandalwood oil, or geraniol. Alternatively, the active can be an insect growth regulator such as hydroprene. Another type of active is a fragrancer or deodorizer/mask. Some of the above oils such as lavender oil fulfill both a repellant and fragrance function.

Yet another type of active is a disinfecting agent such as orthophenyl phenol. These can also perform a deodorizing function in some cases.

Other ingredients (e.g. cosolvent alcohols) may also be included, depending upon the intended application. For example, a furniture polish might include a silicone for providing a shine.

When the spray contains a gaseous propellant and is pressurized in a can, the spray may be sprayed from the aerosol can into the air (in the case of a flying insect killer), or against a surface (in the case of a crawling insect killer or cleaner). As an alternative, a pump spray container (without gas propellant) can be used in a similar manner.

In this latter form, the invention can provide a spray having at least 20% water, at least 0.1% limonene, at least 0.01% butylhydroxytoluene, at least 0.01% alkali metal benzoate, and at least 0.01%, of an active selected from the group consisting of insecticides, insect repellants insect control growth regulators, other fragrances, odor masks, and disinfectants.

An advantage of the present invention is that the sprays are substantially color stable over prolonged periods during storage. This is achieved without adversely impacting the effectiveness of conventional actives or the fragrance, or significantly increasing cost, or preventing the use of an anti-corrosive to protect the can.

These and still other advantages of the present invention will be apparent from the description which follows. In that description reference is made to certain preferred embodiments. However, the claims should be looked to in order to judge the full scope of the invention, and the claims are not to be limited to just the preferred embodiments.

DETAILED DESCRIPTION OF THE PREFERRED EMBODIMENTS

A. Overview

Preferred forms of the present invention are aerosol emulsion sprays with insecticidal active. These typically have water, surfactants, hydrocarbon solvent, propellant gas, and one or more actives. In accordance with the present invention, we also add BHT as an antioxidant to protect the active, limonene as a preferred desired fragrance (and additional solvent), and (in preferred forms) sodium benzoate as a corrosion inhibitor.

B. Examples/Comparative

Ingredients by Weight Percent

| chemical | Formula A | Formula B | Formula C | Formula D | Formula E |
|---|---|---|---|---|---|
| sodium benzoate | 0.20 | — | — | — | — |
| sodium nitrite | — | — | 0.10 | — | 0.10 |
| sorbitan monooleate surfactant | 0.24 | 0.24 | 0.24 | 0.24 | 0.24 |
| stearic acid ETO adduct, 3.5 mols, surfactant | 0.66 | 0.66 | 0.66 | 0.66 | 0.66 |
| Norpar 13 hydrocarbon | 10.39 | 10.39 | 10.39 | 10.39 | 10.39 |

-continued

| chemical | Formula A | Formula B | Formula C | Formula D | Formula E |
|---|---|---|---|---|---|
| neopynamin forte/ tetramethrin | 0.30 | 0.30 | 0.30 | 0.30 | 0.30 |
| permethrin | 0.11 | 0.11 | 0.11 | 0.11 | 0.11 |
| BHT | 0.50 | — | — | 0.50 | 0.50 |
| d-limonene | 1.8 | 1.8 | 1.8 | 1.8 | 1.8 |
| A-46 isobutane/ propane | 36.0 | 36.0 | 36.0 | 36.0 | 36.0 |
| water | 49.8 | 50.5 | 50.4 | 50.0 | 49.9 |
| color change results | | | | | |
| after 27 days | clear | clear | yellow tinge | yellow tinge | golden |
| number rating 0-5 | 0 | 0 | 1 | 2 | 5 |

C. Test Data

With respect to formulas A-E, one ("A") had both BHT and sodium benzoate, one had neither and no sodium nitrite ("B"), one had neither plus sodium nitrite ("C"), one had BHT and neither sodium nitrite or sodium benzoate ("D"), and one had BHT plus sodium nitrite with no sodium benzoate ("E") . The formulas were stored in a standard, albeit glass, aerosol container. I observed discoloration by visual observation technique as well as a subjective 0-5 ranking system with 5 being assigned to the sample with the most discoloration and 0 to the sample with no coloration, in each case after a 27 day simulated storage period.

While Formula B, without BHT and corrosion inhibitor is clear, when BHT was added (Formula D) there was discoloration even in the absence of corrosion inhibitor, which was similar in intensity to Formula C containing only sodium nitrite (and no BHT or sodium benzoate). When both sodium nitrite and BHT were added (Formula E), discoloration was even more intense. Surprisingly, when sodium benzoate replaced the sodium nitrite, as shown in Formula A, there was essentially no appreciable discoloration of the formula.

Thus, the presence of the three elements (limonene, BHT, alkali metal benzoate) act synergistically, while providing a desired fragrance and corrosion inhibition. Importantly, this is achieved without significant interference to insecticidal activity, and at acceptable cost.

An alternative formulation designed for a non-aerosol pump spray is as follows (ingredients by weight percent):

| chemical | Formula F |
|---|---|
| sodium benzoate | 0.20 |
| Triton X-193 | 3.0 |
| neopynamin forte/tetramethrin | 0.30 |
| permethrin | 0.11 |
| BHT | 0.50 |
| d-limonene | 1.8 |
| water | 94.09 |

While the above describes a number of preferred embodiments of the present invention, it will be appreciated that other embodiments are also within the scope of the invention. For example, other alkali metal benzoates should also be beneficial in combination with BHT. Moreover, the invention should also be useful with other actives. Thus, the claims which follow should be looked to in order to judge the full scope of the invention.

INDUSTRIAL APPLICABILITY

The present invention provides improved aerosol sprays, particularly those that deliver insecticides, where the spray contains limonene and is resistant to discoloration during storage.

I claim:

1. An aerosol spray, comprising:
   at least 20% water by weight;
   at least 1% hydrocarbon solvent by weight;
   at least 0.1% surfactant by weight;
   at least 0.1% limonene by weight;
   at least 0.01% butylhydroxytoluene by weight;
   at least 0.01% alkali metal benzoate by weight; and
   at least 0.01%, by weight, of an active selected from the group consisting of synthetic pyrethroid insecticides and natural pyrethrum insecticides;
   wherein the spray is formulated so as to be capable of resisting discoloration if stored for a period of 27 days.

2. A spray, comprising:
   at least 20% water by weight;
   at least 0.1% limonene by weight;
   at least 0.01% butylhydroxytoluene by weight;
   at least 0.01% alkali metal benzoate by weight; and
   at least 0.01%, by weight, of an active selected from the group consisting of synthetic pyrethroid insecticides and natural pyrethrum insecticides;
   wherein the spray is formulated so as to be capable of resisting discoloration if stored for a period of 27 days.

3. The aerosol spray of claim 1, wherein the spray further comprises a propellant.

4. The aerosol spray of claim 3, wherein the spray is an aerosol emulsion spray and the propellant is a mixture of isobutane and propane.

5. The aerosol spray of claim 1, wherein the hydrocarbon solvent has between 6 and 12 carbons.

6. The aerosol spray of claim 1, wherein the benzoate is sodium benzoate.

7. The aerosol spray of claim 1, wherein the spray is an insecticidal emulsion.

8. The aerosol spray of claim 7, wherein the spray is an aerosol insecticidal emulsion.

9. The aerosol spray of claim 6, wherein the spray does not include sodium nitrite.

* * * * *